(12) United States Patent
Adden et al.

(10) Patent No.: US 9,801,801 B2
(45) Date of Patent: Oct. 31, 2017

(54) GLYOXAL-FREE CELLULOSE DERIVATIVES FOR PERSONAL CARE COMPOSITIONS

(71) Applicant: Dow Global Technologies LLC, Midland, MI (US)

(72) Inventors: Roland Adden, Walrode (DE); Tatiana Drovetskaya, Basking Ridge, NJ (US); Emmett Partain, III, Bound Brook, NJ (US)

(73) Assignee: Dow Global Technologies LLC, Midland, MI (US)

( * ) Notice: Subject to any disclaimer, the term of this patent is extended or adjusted under 35 U.S.C. 154(b) by 1 day.

(21) Appl. No.: 14/433,896

(22) PCT Filed: Oct. 2, 2013

(86) PCT No.: PCT/US2013/063016
§ 371 (c)(1),
(2) Date: Apr. 7, 2015

(87) PCT Pub. No.: WO2014/058670
PCT Pub. Date: Apr. 17, 2014

(65) Prior Publication Data
US 2015/0258002 A1  Sep. 17, 2015

Related U.S. Application Data

(60) Provisional application No. 61/712,493, filed on Oct. 11, 2012.

(51) Int. Cl.
| | | |
|---|---|---|
| A61K 8/73 | (2006.01) |
| A61K 8/41 | (2006.01) |
| A61K 8/46 | (2006.01) |
| A61Q 5/02 | (2006.01) |
| A61Q 19/10 | (2006.01) |

(52) U.S. Cl.
CPC .............. A61K 8/731 (2013.01); A61K 8/41 (2013.01); A61K 8/463 (2013.01); A61K 8/466 (2013.01); A61Q 5/02 (2013.01); A61Q 19/10 (2013.01); A61K 2800/30 (2013.01); A61K 2800/596 (2013.01)

(58) Field of Classification Search
None
See application file for complete search history.

(56) References Cited

U.S. PATENT DOCUMENTS

| | | | |
|---|---|---|---|
| 3,396,034 A | 8/1968 | Blondheim et al. | |
| 4,557,938 A | 12/1985 | Sander et al. | |
| 4,671,823 A | 6/1987 | Shah et al. | |
| 4,735,659 A | 4/1988 | Bishop | |
| 5,258,429 A * | 11/1993 | Kniewske | C08L 1/26 524/31 |
| 5,266,334 A | 11/1993 | Phadke et al. | |
| 5,869,029 A | 2/1999 | Graff-Andersen et al. | |
| 6,197,100 B1 | 3/2001 | Melbouci | |
| 6,258,342 B1 | 7/2001 | Harcum et al. | |
| 2003/0139502 A1* | 7/2003 | Ricca | A61K 8/463 524/156 |
| 2006/0069193 A1* | 3/2006 | Hayakawa | B01F 7/022 524/322 |
| 2007/0175361 A1 | 8/2007 | Bonney et al. | |
| 2010/0132132 A1* | 6/2010 | Zhang | A61K 8/442 8/406 |
| 2010/0291272 A1 | 11/2010 | Steffens et al. | |
| 2011/0064683 A1* | 3/2011 | Jordan | A61K 8/8147 424/63 |
| 2011/0112328 A1 | 5/2011 | Drovetskaya et al. | |
| 2013/0102787 A1* | 4/2013 | Hagihara | C07D 401/04 546/275.7 |

FOREIGN PATENT DOCUMENTS

| | | |
|---|---|---|
| EP | 0198094 A1 | 10/1986 |
| EP | 2371347 A2 | 10/2011 |
| EP | 2371348 A2 | 10/2011 |
| GB | 791315 A | 2/1958 |
| GB | 1165824 A | 10/1969 |
| JP | 2007176800 A | 7/2007 |

OTHER PUBLICATIONS

Peng et al., "Chemistry and Applications of Nanocrystalline Cellulose and its Derivatives: A Nanotechnology Perspective" Can J Chem Eng 9999:1 (2011).*

* cited by examiner

*Primary Examiner* — Robert A Wax
*Assistant Examiner* — Thor Nielsen
(74) *Attorney, Agent, or Firm* — Edward L. Brant

(57) ABSTRACT

The present application describes personal care compositions, comprising a surfactant and agglomerated cellulose derivative, provided that the cellulose derivative has been agglomerated with a sufficient amount of carboxymethylcellulose as binder, and provided that the personal care composition is substantially free of glyoxal.

9 Claims, No Drawings

GLYOXAL-FREE CELLULOSE DERIVATIVES FOR PERSONAL CARE COMPOSITIONS

CROSS-REFERENCE TO RELATED APPLICATION(S)

This application claims priority to and is a 371 U.S.C. §371 national phase application of International Application No. PCT/US13/063016, filed on Oct. 2, 2013, which claims the priority benefit of U.S. Provisional Application No. 61/712,493, filed on Oct. 11, 2012, each of which is incorporated herein by reference in its entirety.

FIELD

The present application relates to methods for producing glyoxal-free cellulose derivatives and personal care compositions containing the same.

BACKGROUND

Cellulose derivatives confer many important benefits to personal care compositions, including, depending on which cellulose derivative is selected, thickening, sensorial benefits, foam enhancement, SPF boost, and many others. One common problem among the water-soluble cellulose derivatives is getting them in solution, which requires sufficient dispersion and hydration. Dispersion refers to spreading of particles or groups of polymer chains throughout a solution. Hydration refers to loosening of the polymer chains and expansion of their hydrodynamic volume (and corresponding viscosity buildup). If dispersion is poor, or if hydration outpaces dispersion, hydrated polymer can swell and isolate relatively dry, non-hydrated polymer from the solution, forming lumps. Desirable dispersion and hydration are normally characterized by little to no lump formation and a rapid viscosity build up over time, respectively.

Accordingly, it has long been a goal in the industry to produce water-soluble cellulose derivatives which are readily dispersible and hydrate quickly in aqueous solutions, more particularly at room temperature. To this end, those skilled in the art have added wetting agents or other adjuvants to water-soluble cellulose derivatives to improve dispersion and hydration, the most widely adopted technique being treatment with glyoxal, or glyoxal and sodium tetraborate. However, like many dialdehydes, glyoxal, in high amounts, is harmful to health and is considered to lack environmental compatibility. In some cases, there may be requirements to identify these compounds with hazard symbols.

Therefore, what is needed are water-soluble cellulose derivatives that are glyoxal-free, yet are readily dispersible and hydrate quickly in aqueous solutions, characterized by little to no lump formation and a relatively rapid viscosity build up over time.

DETAILED DESCRIPTION

In one embodiment, the present invention provides personal care composition, comprising a granulated or agglomerated cellulose derivative, provided that the cellulose derivative has been granulated or agglomerated with a sufficient amount of carboxymethylcellulose as binder; provided that the personal care composition is substantially free of glyoxal.

"Substantially free of" means less than 0.001 wt. %, preferably less than 0.0001 wt. %, and more preferably, less than 1 ppm.

"Personal care" relates to compositions to be topically applied to a person (including mouth, ear, and nasal cavities, but not ingested). Such compositions must be cosmetically acceptable, that is, contain ingredients typically used in personal care compositions, and this is intended to underscore that materials that are toxic when present in the amounts typically found in personal care compositions are not contemplated as part of the present invention.

In one embodiment, the personal care composition further comprises a surfactant, and is a personal care cleansing composition. "Personal care cleansing compositions" include skin care cleansing compositions (such as facial cleansers, rinse off lotions, and body wash), hair cleansing compositions (i.e., shampoos), and oral cleansing compositions (such as toothpaste, mouthwash, and chewing gum).

"Surfactant" refers to any cosmetically acceptable cationic, anionic, nonionic, or amphoteric surfactant, or a mixture thereof. In one embodiment, the surfactant is a detergent surfactant. In this embodiment, the surfactant is present in an amount from about 5 wt % to about 25 wt % by weight of the composition, preferably from about 5 wt % to about 20 wt % by weight of the composition, most preferably from about 7 wt % to about 18 wt % by weight of the composition.

Preferably, the detergent surfactant is an anionic surfactant, more preferably in combination with an amphoteric surfactant. In one embodiment, the anionic surfactant is ammonium laureth sulfate, ammonium lauryl sulfate, sodium laureth sulfate, or sodium lauryl sulfate.

In one embodiment, the mixture is an anionic surfactant in combination with a second surfactant that is disodium cocoamphodiacetate, decylglucoside, or cocamidopropyl betaine. In one embodiment, the second surfactant is present in an amount from about 1 wt % to about 10 wt %, preferably from about 1 wt % to about 8 wt %, more preferably from about 2 wt % to about 6 wt %, by weight of the composition.

In a preferred embodiment, the surfactant is a mixture of sodium laureth sulfate (such as is commercially available from Cognis as under the tradename STANDAPOL ES) and disodium cocoamphodiacetate (such as is commercially available from Henkel as under the tradename VELVETEX CDC). When the surfactant is a mixture of sodium laureth sulfate and disodium cocoamphodiacetate, the ratio of sodium laureth sulfate to disodium cocoamphodiacetate is in a range from about 9:1 to about 2:1, most preferably about 6:1.

"Cellulose derivative" does not include cellulose or microcrystalline cellulose. Cellulose is a linear, unbranched polysaccharide composed of anhydroglucose monosaccharide units linked through their 1,4 positions by the β anomeric configuration. Substitution of the hydroxyl groups (with positions at 2, 3, or 6) will yield cellulose derivatives. Common substitutions include methyl (methylcellulose), ethyl (ethylcellulose), hydroxyethyl (hydroxyethylcellulose), hydroxypropyl (hydroxypropylcellulose), and mixtures thereof, such as hydroxypropyl methylcellulose. The theoretical limit of hydroxyl substitution is three. As not every anhydroglucose unit will be substituted identically, the average number of hydroxyl groups substituted per anhydroglucose unit is referred to as the degree of substitution, i.e., as a mean over the whole polymer chain.

In one embodiment, the cellulose derivative is methylcellulose. Methylcellulose is generally available under the tradename METHOCEL A (The Dow Chemical Company). The polymeric backbone of cellulose is a repeating structure of anhydroglucose units. Treatment of cellulosic fibers with caustic solution and methyl chloride, yields cellulose ethers substituted with methoxy groups. The term "DS" refers to the degree of methoxyl substitution per anhydroglucose unit. Methylcellulose typically has a DS of about 1.4 to about 2.5, preferably about 1.5 to about 2.2, more preferably about 1.8. In one embodiment, the methylcellulose has a viscosity at 2% concentration in water at 20° C., of about 1 cps to about 100,000 cps, preferably about 5 cps to about 40,000 cps. In one embodiment, the viscosity is about 4000 cps, in another embodiment, the viscosity is about 15 cps.

In one embodiment, the cellulose derivative is hydroxypropyl methylcellulose. Hydroxypropyl methylcellulose is generally available under the tradename METHOCEL E, F, J, and K (The Dow Chemical Company). The polymeric backbone of cellulose is a repeating structure of anhydroglucose units. Treatment of cellulosic fibers with caustic solution and methyl chloride and propylene oxide, yields cellulose ethers substituted with methoxy groups and hydroxypropyl groups. The term "DS" refers to the degree of methoxyl substitution per anhydroglucose unit. The term "MS" refers to the degree of hydroxypropoxyl substitution per anhydroglucose unit. Each grade is differentiated by the methoxy and hydroxypropyl substitution on the polymeric backbone. Hydroxypropyl methylcellulose useful in the present invention has a DS of less than 2.0, preferably, the DS is about 1.8 or about 1.4, and an MS in a range of about 0.05 to about 1.2, preferably about 0.1 to about 0.5.

In one embodiment, the cellulose derivative is hydroxylethyl cellulose, generally available under the tradename CELLOSIZE (The Dow Chemical Company).

Terminal hydroxyl groups of substituents may further be substituted.

In one embodiment, the cellulose derivative is hydroxylethyl cellulose further substituted with a quaternary amine (for example, by alkylating hydroxyethyl cellulose with either glycidyl trimethylammonium chloride or 3-chloro-2-hydroxypropyltrimethylammonium chloride) to form permanently charged cationic cellulose derivatives (including polyquatemiums, PQ-10, PQ-24, and PQ-67), generally available under the tradenames SOFTCAT or UCARE (The Dow Chemical Company).

Alternatively, pH dependent charged cationic cellulose derivatives, such a tertiary amine substituted cellulose derivative, are possible, for example, by adding N,N-diethylaminoethyl chloride hydrochloride to hydroxyethylcellulose (although other cellulose derivatives are contemplated as well).

Cellulose derivatives are normally sold in solid, dry form, and hence their powder handling and processing properties are extremely important. For example, a low dust content is desirable for dry cellulose derivatives. The ability of the dry cellulose derivative to be poured from a container or receptacle is described as flowability. Flowability is affected by particle shape and size distribution, and resulting bulk density. Bulk density is the mass of powdered solid material per unit of volume occupied. Acceptable flowability generally depends upon relatively high bulk density and relatively low angle of repose. The angle of repose is the maximum angle between the slope of a conical discharged pile of powder and the surface it rests upon, a lower angle representing a more widely spread pile.

Often, it is desirable to put cellulose derivatives in solution as part of use for various applications. It has long been a goal in the industry to produce cellulose derivatives which are readily dispersible and hydrate relatively quickly in aqueous solutions, more particularly at room temperature. Desirable dispersion and hydration are normally characterized by little to no lump formation and a relatively rapid viscosity build up over time, respectively.

Accordingly, it is a critical feature of the present invention that the cellulose derivative be granulated or agglomerated. In contrast to cellulose derivative material that has been prepared but not further processed, the term "granulated or agglomerated" refers to cellulose derivative that has been treated, as will be described, with carboxymethyl cellulose ("CMC") in a high shear mixer to exhibit improved dispersibility in aqueous solutions.

CMC is a cellulose derivative formed by treating cellulose fibers with caustic solution, followed by chloroacetic acid (i.e., to form cellulose ethers substituted with carboxymethyl groups).

In one embodiment, the cellulose derivative is granulated. US Patent Publication 2007/0175361, the entirety of which is incorporated herein by reference, teaches a process of making cold-water dispersible cellulose derivatives by introducing a particulate, water-soluble polymer and an aqueous solution comprising a surface treatment additive into a high shear mixing chamber prior to being introduced into a pneumatic drying means, for example, in a fluid bed agglomerator, and maintaining the particulate, water-soluble polymer suspended in a gas carrier within a chamber of the pneumatic drying means, maintaining the gas carrier at a temperature below the temperature at which the water soluble polymer particles degrade or become "sticky" and agglomerate to leave residual, dried surface treatment additive coated on the particulate, water-soluble polymer in an amount sufficient to produce the cold water dispersible water-soluble polymer. This makes a cellulose derivative more dispersible in aqueous solutions at room temperature and improves hydration, however, this has the deleterious effect of lowering the bulk density and increasing the angle of repose, which in turn decreases flowability.

Typically, those skilled in the art seek to minimize agglomeration and encourage granulation as discussed above. It has now been surprisingly found that the present process can achieve excellent results by proceeding contrary to the conventional wisdom.

Accordingly, in the preferred embodiment, the cellulose derivative is agglomerated. In this process for producing an aqueous dispersible cellulose derivative, cellulose derivative that has been prepared, but not subjected to further processing (like addition of glyoxal) is introduced into a high shear mixer, with at least 20 percent water by weight, and an additional about 0.5 to about 3 weight percent, preferably 2.5 weight percent, of carboxymethyl cellulose is added to the mixer (preferably, the CMC is in solution with the water), thereby forming cellulose derivative agglomerates. The agglomerates are dried by non-contact drying means to form the aqueous dispersible cellulose derivative. It has been surprisingly found that the present process can achieve excellent results without additional surface treatment additives, for example, salts, sugars, surfactants, and/or dialdehydes.

Contemplated high shear mixers include ring layer mixers, Ploughshare mixers, Schugi mixers, and Turbulizer mixers. In a preferred embodiment, the high shear mixer is a ring layer mixer. A ring layer mixer generally comprises a horizontal drum with a mixing shaft axially disposed in it. The mixing shaft has blades, bolts, and/or paddles protruding from it. Mixing shaft geometry can create various mixing zones for transporting, dispersing, mixing, and the like. The product to be mixed forms a concentric ring via centrifugal force, and moves through the mixer in plug-like flow. Liquid is added through a hollow shaft or by injection through special perforated mixing tools. The residence time varies with rpms, flow rate, amount of material, drum length, and selected mixing shaft geometry. A suitable ring layer mixer can be procured from Loedige (Paderborn, Germany), under the tradename CORIMIX CM 20. In an alternative embodiment of the present invention, the high shear mixers can be replaced by a flow jet mixer.

In one embodiment, the process further comprises adjusting the residence time in the ring layer mixer, for example, rpms and mixing shaft geometry, to encourage agglomeration of the cellulose derivative. In one embodiment, the process further comprises adjusting the spray rate and residence time in the ring layer mixer to discourage granulation of the cellulose derivative.

In one embodiment, after drying, the aqueous dispersible cellulose derivative has about 0.25 to about 2.0 weight percent CMC, and preferably less than 1 weight percent CMC. The term "aqueous dispersible cellulose derivative" refers to a cellulose derivative which exhibits improved dispersibility in aqueous solutions compared to cellulose derivative that has been prepared, but not subjected to further processing. In a preferred embodiment, the introduction step is in a continuous process, but the process may be carried out in a batch or semi-batch process in alternative embodiments.

Some cellulose derivative chemical features, like degree of substitution, remain constant throughout the process. Physical features of the cellulose derivative, however, will be changed by the currently described process. Cellulose derivative that has been prepared, but not subjected to further processing, for example, methylcellulose has a bulk density of about 150 g/L to about 350 g/L, preferably about 220 to about 240 g/L, and an angle of repose of about 46 to about 51, preferably about 47.5° to about 49.0°, and thus has good flowability, however, it is not generally considered dispersible in aqueous solutions at room temperature and is very slow to hydrate, and also retains a large percentage of dust, i.e., over 50% particles with particle size of 63 micron or less. Hydroxypropyl methylcellulose that has been prepared, but not subjected to further processing, has a bulk density of about 200 g/L to about 600 g/L.

The step of drying the agglomerates by non-contact drying means, in one embodiment, includes those where the non-contact drying means is a fluid bed dryer. In one embodiment, the present invention provides a further step, comprising drying the cellulose derivative at a temperature of more than about 50° C., preferably about 70° C. Alternatively, the cellulose derivative is dried to a residual water content of less than about 10% by weight, irrespective of temperature.

In one embodiment, the aqueous dispersible cellulose derivative disperses well with minimal lumps visible. In one embodiment, the aqueous dispersible cellulose derivative hydrates relatively quickly, as evidenced by improved times to 90% viscosity (the time in min where the given % of the final torque was obtained). As can be appreciated, higher viscosity cellulose derivatives may hydrate slower than this while still showing good performance in applications.

In one embodiment, the aqueous dispersible cellulose derivative has a bulk density that is at least 90%, preferably at least 92%, preferably at least 93%, and most preferably at least 94% of the bulk density of the cellulose derivative before agglomeration.

In one embodiment, the aqueous dispersible cellulose derivative has an angle of repose that is only 5% greater than, and preferably substantially the same as, or more preferably, less than the angle of repose of the cellulose derivative before agglomeration.

In one embodiment, the aqueous dispersible cellulose derivative has significantly reduced dust, preferably containing less than 30% particles with less than a 64 micron particle size, more preferably less than 25%, and most preferably, less than 22% than the cellulose derivative before agglomeration.

The amount of aqueous dispersible cellulose derivative to be used in personal care compositions is readily determined by those skilled in the art. In one embodiment, the amount of carboxymethylcellulose in the personal care composition is about 0.02 weight percent, while the amount of cellulose derivative is about 2 weight percent.

EXAMPLES

The following examples are for illustrative purposes only and are not intended to limit the scope of the present invention.

Determination of DS and MS

The determination of the % methoxyl and % hydroxypropoxyl in hydroxypropyl methylcellulose is carried out according to the United States Pharmacopeia (USP 32). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion.

Solution Viscosity

The viscosities of aqueous solutions of cellulose ether were measured using a Viscotester VT 550 rotational viscometer supplied by Thermo Haake at 20° C. Unless otherwise mentioned, the constant shear rate of the viscometer was 2.55 second$^{-1}$ using a MV2 rotor and a MV measuring cup with a tempering jacket.

Particle Size Distribution of Cellulose Ether

The particle size distribution of cellulose ether was measured by a circular and horizontal vibration type sieving machine with a specified set of sieves, ISO 3310, Part 1. 50 grams (g) of cellulose ether were sieved using the set of sieves whose mesh sizes correspond to the required particle sizes. The sieve fractions are weighed and the percentage particle size distribution is calculated accordingly. The dust content is the fraction smaller than 63 microns after sieving the cellulose ether accordingly.

Bulk Density

The untapped bulk density of cellulose ether was determined by weighing the contents of a known volume beaker completely filled with cellulose ethers. Values given are average values of three measurements.

Time to 95% Viscosity Build-Up

The viscosity build-up of cellulose ether was measured by analyzing the torque over the time (using a Viscotester VT 550 rotational viscometer from Thermo Haake) at 400 revolutions per minute (rpm) for 30 minutes. Time to 95% viscosity build-up was defined as the time in minute where 95% of the final torque was obtained.

Cellulose ether was dispersed in water at 20+/−0.5° C., and stirred at 400 rpm with a paddle shaped stirrer (Thermo Haake, order number 807-0505, rotor, paddle-shaped) to form 200 g of an aqueous solution with the following concentration: If cellulose ether has a solution viscosity as a one weight percent aqueous solution of more than 1,000 mPa·s, a one weight percent solution of the cellulose ether will be prepared in this test. If cellulose ether has a solution viscosity as a one weight percent aqueous solution of less than 1,000 mPa·s, a two weight percent solution of the cellulose ether will be prepared in this test. After dispersing the cellulose ether in water, the torque was immediately measured at a rate of 20 datapoints per minute for 30 minutes before stopping the test. Torque data of the last 5 minutes of the measurement were averaged and defined as the final torque value. Standard deviation of the torque data of the last 5 minutes of the measurement was calculated. If the standard deviation is larger than 3%, it indicates that a constant final torque value has not been reached. In this case, the time to 95% viscosity build-up is defined as ">30 minute". If the standard deviation is less than 3%, the time to 95% viscosity build-up was defined as the time in minute where 95% of the final torque was obtained.

Example 1—Ring Layer Mixer

Exemplary aqueous dispersible methylcellulose and hydroxypropyl methylcellulose according to the present invention are created as follows. The starting material (raw MC or HPMC) is fed continuously in the ring-layer mixer (CORIMIX CM 20) running at a flow rate of approximately 3000 rpm. Alternatively, acceptable residence time can be achieved by adjusting tip speed or Froude number. 2.5% CMC in water solution is sprayed in the mixer on to the product. Older systems use injection of the water through the jacket, whereas newer systems spray through the fast rotating axle. Sufficient solution is added so that the wetted agglomerate leaving the mixer has a moisture content of approximately 25-30%. The obtained agglomerate is subsequently dried in a fluid bed dryer (Huettlin Mycrolab) at an air inlet temperature of 50-120° C., preferably 70° C., until the product has reached a temperature of approximately 52-53° C. A summary of conditions is recited in TABLE 1.

TABLE 1

| | 2.5% CMC in Water Solution (%) | RLM rpm | RLM CE flow (kg/h) | Drying Temp (° C.) |
|---|---|---|---|---|
| Batch 1 (15 cps MC; DS ~1.8) | 30 | 3000 | 150 | 75 |
| Batch 2 (4000 cps MC; DS ~1.8) | 30 | 3000 | 150 | 75 |
| Batch 3 (50 cps HPMC; DS ~1.8; MS ~0.2) | 30 | 3000 | 150 | 70 |

TABLE 1-continued

| | 2.5% CMC in Water Solution (%) | RLM rpm | RLM CE flow (kg/h) | Drying Temp (° C.) |
|---|---|---|---|---|
| Batch 4 (4000 cps HPMC; DS ~1.8; MS ~0.2) | 30 | 3000 | 150 | 70 |
| Batch 5 (4000 cps HPMC; DS ~1.4; MS ~0.25) | 30 | 3000 | 150 | 75 |

Example 2—Fluid Bed

Exemplary aqueous dispersible methylcellulose and hydroxypropyl methylcellulose according to an alternative process of the present invention are created as follows. The starting material is the same as Example 1, but made in a batch process in a fluid bed processor. After conventionally fluidizing the material, 2.5% CMC in water solution is top sprayed through a nozzle on the fluidized material. The air inlet temperature is held constant at approximately 50° C. during spraying while the product temperature is approximately 35° C. The addition of solution is stopped when the ratio of added solution/(sum of added solution and MC or HPMC) is 0.25 or 0.3. The obtained agglomerate is subsequently dried in a fluid bed dryer (Huettlin Mycrolab) at an air inlet temperature of 70° C. until the product has reached a temperature of approx. 52-54° C. A summary of conditions is recited in TABLE 2.

TABLE 2

| | 2.5% CMC in Water Solution (%) | FBA air inlet (° C.) | FBA product (° C.) | Drying Temp (° C.) |
|---|---|---|---|---|
| Batch 6 (15 cps MC) | 30 | 50 | 32 | 75 |
| Batch 7 (4000 cps MC) | 30 | 50 | 31 | 75 |
| Batch 8 (50 cps HPMC) | 30 | 50 | 31 | 70 |
| Batch 9 (4000 cps HPMC) | 30 | 50 | 31 | 70 |
| Batch 10 (4000 cps HPMC) | 30 | 50 | 32 | 75 |

Example 3

Batches 1-10 were created substantially according to the protocols of Examples 1 and 2, and are characterized with the results being recited in TABLE 3.

TABLE 3

| | Bulk density (g/L) | Dust (% ≤63 μm) | Angle of repose (°) | Dispersibility | Powder Flow (g/min) | Time to 90% visc. (min) |
|---|---|---|---|---|---|---|
| Batch 1 | 226.5 | 20.2 | 47.6 | good | 24 | 4.5 |
| Batch 2 | 213.8 | 24.3 | 49.0 | acceptable | 24 | 17 |
| Batch 3 | 368.6 | 5.7 | 38.5 | good | 189 | 3.5 |
| Batch 4 | 309.7 | 29.5 | 45.8 | acceptable | 36 | 19 |
| Batch 5 | 328.8 | 10.9 | 42.2 | acceptable | 208 | 13 |
| Batch 6 | 116.8 | 12.4 | 52.6 | good | 19 | 4.2 |
| Batch 7 | 85.6 | 6.4 | 50.2 | acceptable | 7 | 5 |
| Batch 8 | 340.3 | 2.7 | 37.7 | good | 241 | 3 |
| Batch 9 | 167.1 | 17.2 | 53.5 | good | 26 | 7 |
| Batch 10 | 205.7 | 6.6 | 45.2 | acceptable | 96 | 13 |

The differences regarding the dispersibility are due to the MC or HPMC viscosity (higher molecular weights tend to disperse somewhat slower). Also, Batches 2 and 7, and Batch 5 and 10, represent grades that show thermodynamically a slower dispersion at 20° C.

The bulk density is determined by weighing a completely filled beaker of known volume. Values given are average values of three measurements. The dust content is the fraction smaller than 63 µm after sieving the product accordingly.

The angle of repose is determined with a Hosokawa Micron Powder Characteristics Tester (model PT-R, 1999, software version 1.02) at a vibration adjustment of ~2.5.

The powder flow speed is measured with the same instrument, using the same method and the same vibration adjustment, as flow by weight through the system for 20 seconds. After the flow becomes consistent, three measurements are combined and averaged.

The dispersibility is tested in a beaker, 0.5 g of the final product is dispersed in a beaker containing 49.5 g water (yielding a 1 weight % solution) stirring at 500-750 rpm. Directly after dispersion, a visual assessment is made by a trained technician to determine the quality of the solution, whether lumps can be seen, and how well the sample is distributed throughout the entire solution. The viscosity build up is measured by analyzing the torque over the time (using a Haake VT 550 viscometer) at 600 rpm for 30 min. The torque data of the last 5 min of the measurement were averaged and defined as final torque level. 90% viscosity build up was defined as the time in min where 90% of the final torque was obtained.

Example 4

An exemplary and a comparative clear facial cleansing composition are listed in TABLE 4 in wt. %.

TABLE 4

|  | Comparative Batch A | Batch 11 |
|---|---|---|
| STANDAPOL ES2 Sodium Laureth Sulfate | 17.5 | 17.5 |
| MACKANATE EL Disodium Laureth Sulfosuccinate | 7 | 7 |
| KESSCO PEG 6000 PEG 150 Distearate | 0.25 | 0.25 |
| SOFTCAT SK-L (2% SOL) Polyquaternium 67 | 12.5 | 12.5 |
| Glyoxalated METHOCEL E4M (5% SOL) HPMC | 5 | — |
| AGGLOMERATED E4M (5% SOL) HPMC | — | 5 |
| GLYDANT DMDM Hydantoin | 0.4 | 0.4 |
| NaCl | 0.1 | 0.1 |
| Water | 57.25 | 57.25 |

Agglomerated E4M HPMC was prepared substantially as described in Example 1. To prepare the personal care compositions, mix water and surfactants until uniform. Add the cellulose derivative solutions and mix until clear. Heat to 65-70° C., then add PEG 150 DS. Mix until dissolved and uniform. Cool to 40° C. and add DMDM Hydantoin. Adjust pH upwards to 6.2-6.7 w/50% TEA.

Comparative Batch A and inventive Batch 11 both formed clear compositions with comparable pH, viscosity, appearance, and stability over three months. Batch 11 had a quicker viscosity build up, but a longer hydration time (the agglomerated material dissolves quicker than the conventional sample, but the viscosity builds very quickly, requiring slower addition (yet still less than 10 minutes) to prevent lumping). However, Batch 11 has the added benefit of being glyoxal free.

Example 5

An exemplary and a comparative anti-frizz smoothing shampoo composition are listed in TABLE 5 in wt. %.

TABLE 5

|  | Comparative Batch B | Batch 12 |
|---|---|---|
| SOFTCAT SX 1300H (1.5% aq soln) Polyquaternium-67 | 18.7 | 18.7 |
| POLYOX N 750 polyethyleneoxide (1% aq soln) | 5 | 5 |
| Glyoxalated E4M hydroxypropyl methylcellulose (5% aq soln) | 2 | — |
| Agglomerated E4M hydroxypropyl methylcellulose (5% aq soln) | — | 2 |
| STANDAPOL ES -2 Sodium Laureth Sulfate (26% solids) | 60.78 | 60.78 |
| VELVETEX CDC disodium cocoamphodiacetate (50% solids) | 6.92 | 6.92 |
| LEXEMUL EGDS glycol distearate | 2 | 2 |
| DOW CORNING 1664 dimethicone (50%) | 2 | 2 |
| Citric Acid (10% aq soln) | 2.2 | 2.2 |
| GLYDANT DMDM Hydantoin | 0.4 | 0.4 |

Agglomerated E4M HPMC was prepared substantially as described in Example 1. To prepare the personal care compositions, stock solutions are prepared. Mix glycol distearate and surfactants until uniform. Add the cellulose derivative solutions and mix. Heat to 70-75° C., then hold for 45 minutes, add citric acid. Cool to 35° C. and add dimethicone with mixing for 90 minutes. Add the polymer solutions and stir for 60 minutes. Cool to room temperature and add preservative, and optionally, fragrance and/or color.

Comparative Batch B and inventive Batch 12 both formed thick, pearlescent compositions with comparable pH, viscosity, appearance, and stability over two months. Batch 12 had a quicker viscosity build up, but a longer hydration time (the agglomerated material dissolves quicker than the conventional sample, but the viscosity builds very quickly, requiring slower addition (yet still less than 10 minutes) to prevent lumping). However, Batch 12 has the added benefit of being glyoxal free.

The invention claimed is:

1. A personal care composition, comprising:
    a surfactant; and
    agglomerated cellulose derivative, provided that the cellulose derivative has been agglomerated with a sufficient amount of carboxymethylcellulose in aqueous solution as binder;
    provided that the personal care composition is substantially free of glyoxal,
    wherein the amount of carboxymethylcellulose is about 0.02 weight percent, based on the total weight of the composition.

2. The personal care composition of claim 1, wherein the cellulose derivative is methylcellulose.

3. The personal care composition of claim 1, wherein the cellulose derivative is hydroxypropyl methylcellulose.

4. The personal care composition of claim 1, wherein the cellulose derivative is hydroxyethyl cellulose substituted with a quaternary amine.

5. The personal care composition of claim 1, wherein the cellulose derivative has a time to 90% viscosity of 20 minutes or less.

6. The personal care composition of claim 1, wherein the surfactant is a mixture of sodium laureth sulfate and disodium cocoamphodiacetate.

7. A method for providing a personal care composition that is substantially free of glyoxal, comprising:
   incorporating the agglomerated cellulose derivative of claim 1 to the personal care composition as a replacement for any cellulose derivative that has been glyoxylated.

8. The personal care composition of claim 1, wherein the cellulose derivative has a time to 90% viscosity of 10 minutes or less.

9. The personal care composition of claim 1, wherein the cellulose derivative has a time to 90% viscosity of 6 minutes or less.

* * * * *